United States Patent
McLeod

(10) Patent No.: US 7,402,144 B2
(45) Date of Patent: Jul. 22, 2008

(54) NON-INVASIVE METHOD AND APPARATUS FOR TREATING ORTHOSTATIC HYPOTENSION

(76) Inventor: Kenneth J. McLeod, 29 Pine Meadow Rd., Vestal, NY (US) 13850

(*) Notice: Subject to any disclaimer, the term of this patent is extended or adjusted under 35 U.S.C. 154(b) by 449 days.

(21) Appl. No.: 10/491,942

(22) PCT Filed: Oct. 9, 2002

(86) PCT No.: PCT/US02/32226

§ 371 (c)(1),
(2), (4) Date: Apr. 6, 2004

(87) PCT Pub. No.: WO03/030805

PCT Pub. Date: Apr. 17, 2003

(65) Prior Publication Data

US 2004/0204663 A1   Oct. 14, 2004

Related U.S. Application Data

(60) Provisional application No. 60/328,265, filed on Oct. 9, 2001.

(51) Int. Cl.
*A61H 1/00* (2006.01)

(52) U.S. Cl. .......................................... 601/27; 601/49

(58) Field of Classification Search ................... 601/46, 601/48, 49–51, 27
See application file for complete search history.

(56) References Cited

U.S. PATENT DOCUMENTS

| | | | | | |
|---|---|---|---|---|---|
| 3,548,811 | A | * | 12/1970 | Wilson | 601/111 |
| 3,911,907 | A | * | 10/1975 | Smith, Jr. | 482/1 |
| 5,273,028 | A | * | 12/1993 | McLeod et al. | 601/35 |
| 5,484,388 | A | * | 1/1996 | Bassett et al. | 601/27 |
| 5,515,865 | A | * | 5/1996 | Scanlon | 600/534 |
| 5,941,807 | A | * | 8/1999 | Cassidy et al. | 482/146 |

* cited by examiner

*Primary Examiner*—Michael A. Brown
(74) *Attorney, Agent, or Firm*—Carter, DeLuca, Farrell & Schmidt, LLP

(57) ABSTRACT

A non-invasive method and apparatus are provided for treating orthostatic hypotension and for reducing the effects caused there from. An increase in blood and fluid flow in the lower extremities is achieved by vibrating the lower body of the individual at a frequency in the range of 10-120 Hz. The apparatus includes a strap for being secured to a body part of the individual's lower extremities, e.g., the sole of one's foot, and a displacement sensor which senses any movement of the body part. The displacement sensor continuously sends signals to a processor of the apparatus which indicate whether there was any movement of the body part. If the displacement sensor did not sense any substantial movement of the body part for a predetermined period of time the processor sends a signal to a vibrating mechanism. The signal activates the vibrating mechanism causing vibration of the body part for increasing blood and fluid flow in the lower extremities. The vibrating mechanism causes vibration for a predetermined period of time.

9 Claims, 6 Drawing Sheets

NON-INVASIVE METHOD AND APPARATUS FOR TREATING ORTHOSTATIC HYPOTENSION

PRIORITY

This application is based on and claims priority to U.S. Provisional Application No. 60/328,265 filed on Oct. 9, 2001, the contents of which are incorporated herein by reference.

BACKGROUND

1. Technical Field

This disclosure relates to a medical treatment procedure and apparatus for performing the same. More particularly, the disclosure relates to a non-invasive method and apparatus for treating orthostatic hypotension.

2. Description of the Related Art

Hypotension is manifested as abnormally low blood pressure. Orthostatic hypotension is a condition caused by extended periods of quiet standing or sitting or by sudden changes of position from sitting or lying to a sitting or standing position. The effects of orthostatic hypotension are mainly age-dependent and may include high rate of bone loss and muscle degeneration. These effects are primarily attributed to decreases in blood and fluid flow in the lower extremities when the body is in static upright posture for a prolonged period of time.

It has been shown that the ability of the skeletal muscle pump to contribute to sustaining blood flow varies considerably as a function of age and/or physical status. For example, the data on postmenopausal women indicate that there are subpopulations of women which do not adapt well to orthostasis. It has been demonstrated that declining systolic pressure in the absence of any corresponding significant rise in diastolic pressure and/or pulse rate indicates the potential for significantly decreased blood flow to the lower extremities for many postmenopausal women while in an upright position for a prolonged period of time; a response that is not inconsistent with high rates of bone loss and muscle degeneration.

Current methods of treating orthostatic hypotension include having the individual wear elastic stockings. The individual is generally prescribed elastic stockings if his blood pressure drops more than 20 mm/Hg while in an upright posture, or the individual manifests obvious signs of orthostatic hypotension, e.g., fainting.

Accordingly there exists a need for a non-invasive method and apparatus for treating individuals experiencing orthostatic hypotension, especially individuals in occupational, healthcare, or home settings where extended periods of quiet standing or sitting occurs regularly and could result in significant decreases in bone and muscle loss arising from poor blood circulation and perfusion caused by these static postures.

Therefore, it is an aspect of the present disclosure to provide a non-invasive method and apparatus for treating orthostatic hypotension and for reducing the effects caused from orthostatic hypotension.

SUMMARY

A non-invasive method and apparatus are disclosed for treating orthostatic hypotension and for reducing the effects caused from orthostatic hypotension. The non-invasive method and apparatus are capable of increasing blood and fluid flow in the lower extremities of an individual while the individual is in a static posture, such as in a sitting, standing, or other upright static posture, for a prolonged period of time. An increase in blood and fluid flow in the lower extremities is achieved by vibrating the lower body of the individual at a frequency in the range of 10-120 Hz, and preferably, in the range of 40-60 Hz. The acceleration of vibration is more than about 0.1 g/cycle and less than about 1.0 g/cycle (where g=9.8 m/s$^2$), and preferably 0.1 g/cycle to 0.2 g/cycle, in order to cause the skin surface to be depressed by 10-50 microns. The vibration can be uniform, interrupted, varying in magnitude, etc.

The lower body can be vibrated by having the individual rest on a vibrating platform, such as described in U.S. Pat. Nos. 5,376,065; 5,273,028; 5,190,800; and 5,103,806, the contents of these patents are incorporated herein by reference.

The lower body can also be vibrated by the apparatus of the present disclosure. The apparatus enables the individual to be treated for orthostatic hypotension in many settings, such as occupational, healthcare, or home settings where extended periods of quiet standing or sitting occurs regularly. The apparatus includes a strap for being secured to a body part of the individual's lower extremity, e.g., the sole of one's foot, and a displacement sensor which senses any movement of the body part.

The displacement sensor continuously sends signals to a processor of the apparatus which indicate whether there was any substantial movement, e.g., more than 10 cm, of the body part. If the displacement sensor did not sense any substantial movement of the body part for a predetermined period of time, e.g., five minutes, it is determined that the person is in a substantially static posture and the processor sends a signal to a vibrating mechanism. The signal activates the vibrating mechanism causing vibration of the body part to enhance blood and fluid flow in the lower extremities. The vibrating mechanism could cause vibration of the body part for a predetermined period of time, e.g., two minutes to twenty minutes, or until body motion is detected by the displacement sensor.

Controls on the apparatus enable the individual to select and set the predetermined periods of time and other parameters, such as the frequency that the vibrating mechanism vibrates, as well as to turn off the apparatus. The controls can also be used to bypass the automatic activation of the vibrating mechanism. That is, the controls can be used to cause direct electrical stimulation of the vibrating mechanism, thereby, bypassing the mechanical displacement sensor, allowing a robust response even in the elderly who have lost much, if not most, of their vibro-tactile sensation abilities. It is provided that the controls can be located on a wireless or non-wireless remote control for enabling the individual to easily control the apparatus while in any body position.

It is contemplated for the soles of the feet to be bypassed and the neuromuscular system be stimulated at the level of the Achilles' tendon, triggering skeletal muscle activity. It is further contemplated to stimulate the muscle body itself to directly produce muscle twitching, and therefore, skeletal muscle pump activity.

Potential application of the described method and apparatus is envisioned in occupational, healthcare, or home settings where extended periods of quiet standing or seating is required and which could result in significant decreases in physical and mental fatigue, as well as other pathophysiological responses associated with decreased blood and fluid flow, including, for example, the disuse related bone and muscle loss arising from the poor perfusion caused by these static postures.

Further features of the above embodiments will become more readily apparent to those skilled in the art from the following detailed description of the apparatus taken in conjunction with the drawings.

BRIEF DESCRIPTION OF THE DRAWINGS

Various embodiments will be described herein below with reference to the drawings wherein.

DETAILED DESCRIPTION OF PREFERRED EMBODIMENTS

Figure 1:
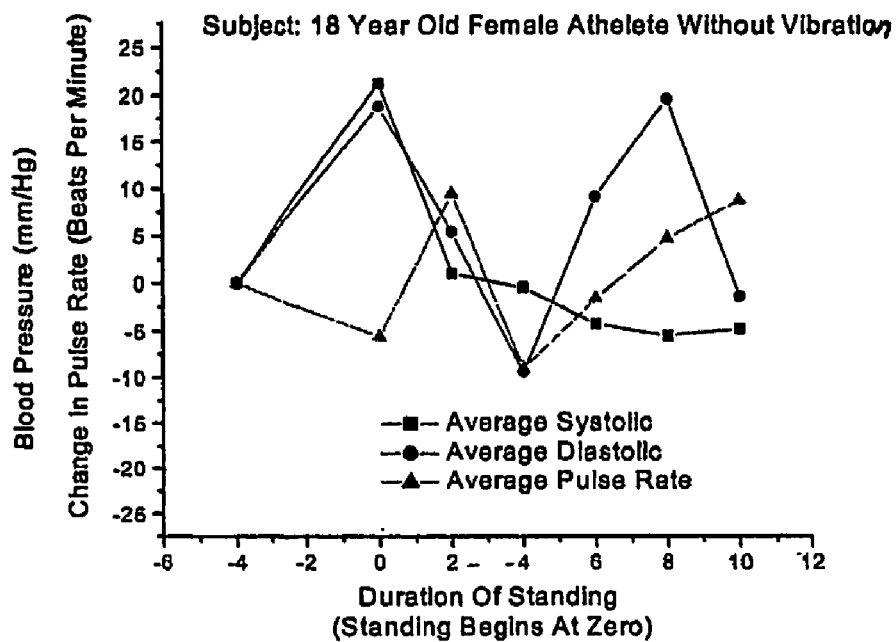
FIGS. 1 and 2 are graphs showing the influence of non-vibration and whole body vibration on several physiologic responses for a young adult female.

The present disclosure describes a non-invasive method and apparatus for treating orthostatic hypotension. Once an individual is determined to be experiencing orthostatic hypotension or that the individual is prone to orthostatic hypotension, the individual can be treated by the method and apparatus of the present disclosure. However, it is understood that the individual can be treated by the method and apparatus of the present disclosure even if there has been no determination made that the individual is experiencing orthostatic hypotension or is prone to orthostatic hypotension.

Before describing the method and apparatus of the present disclosure, a description is provided in how to determine whether an individual is experiencing or likely to experience orthostatic hypotension. Two case studies are presented below which illustrate the influence of vibrating the lower extremities on blood flow during orthostatic stress, i.e., quiet standing, for a young healthy female (age 18) and a postmenopausal female (age 46). The individuals were situated on a vibration platform, such as described in U.S. Pat. Nos. 5,376,065; 5,273,028; 5,190,800; and 5,103,806, the contents of these patents are incorporated herein by reference. The vibration platform was set to vibrate at 37 Hz, 0.2 g (where g=9.8 m/s$^2$)peak-to-peak vertical whole body vibration.

The studies presented below indicate that vibrating the lower extremities during orthostatic stress leads to substantial physiologic responses in the older individual indicative of enhanced blood and fluid flow in the lower extremities, as compared to the physiologic responses without vibration, an indication that the older individual is experiencing orthostatic hypotension. The younger individual does not experience substantial physiologic responses during vibration as compared to non-vibration, an indication that vibration seems to help enhance blood and fluid flow in the lower extremities, but the treatment is not really necessary for the individual.

The physiologic responses recorded for the two individuals during the studies include systolic and diastolic blood pressure, as well as pulse rate. FIGS. 1-4 illustrate the systolic and diastolic blood pressure changes, as well as heart rate changes, for the younger and older individuals in the standing position (standing began at time zero) with hands held at chest height holding a support 16 (see FIG. 5), following ten minutes in the supine position (first data point).

Upon moving from the supine position to an upright sitting or standing, gravitational forces results in a rapid (on the order of a few minutes) pooling of the blood in the lower extremities. In the absence of adequate muscle pump activity (i.e., muscle contractions in the legs) systolic blood pressure will fall due to inadequate refilling of the heart. The heart rate will commonly increase to compensate for the decreased blood volume being pumped per beat, however, this compensation is never complete. Simultaneously, vaso-contraction acts to decrease the vessel volume available for pooling, but this results in an increased diastolic pressure. The inability to adequately undertake these normal physiologic responses to orthostatic stress can have severe repercussions, including dizziness, fainting, muscle fatigue and atrophy, as well as bone atrophy (i.e., osteoporosis), however, essentially everyone experiences some degree of reduced blood and fluid flow during quiet standing and sitting, and therefore, a distinct physiologic stress.

It is noted that each data point in FIGS. 1-4 represents the average of four replications of the study protocol.

As shown by FIG. 1, without vibration, the younger individual's physiologic responses are as follows: following a transient activity, systolic blood pressure begins a slow decrease, consistent with the lower extremity pooling of blood and interstitial fluid. Periodic vaso-constriction results in time-varying diastolic pressures, and heart rate increases slightly. These physiologic responses are indicative of adequate blood blow to the lower extremities, i.e., these physiologic responses are inconsistent from those indicative of orthostatic hypotension.

Figure 2:
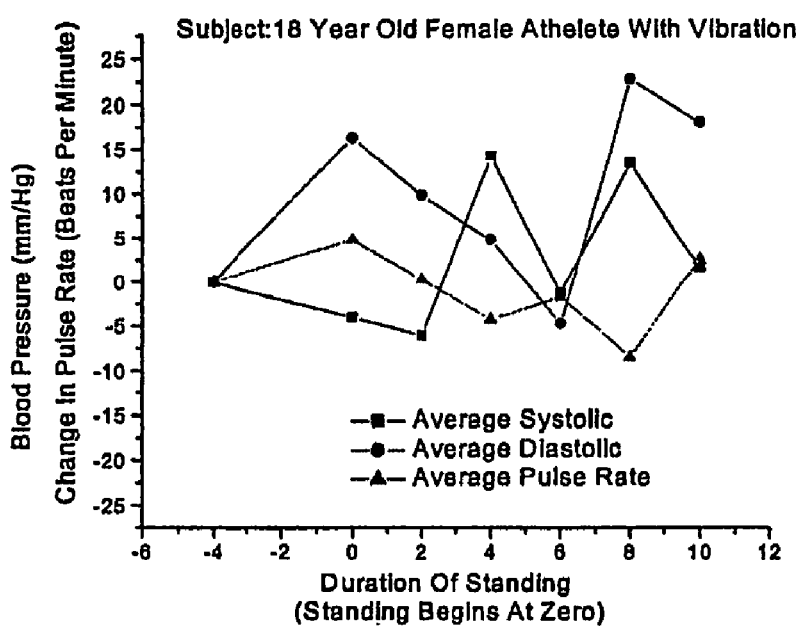

With reference to FIG. 2, whole body vibration has a small, but clearly evident effect on the physiologic response to orthostatic stress in the young adult female. The drop in systolic blood pressure is eliminated, and as a result, heart rate is maintained at or below supine levels. Accordingly, the young adult female is not experiencing and is not likely to experience orthostatic hypotension from maintaining a static posture.

Figure 3:
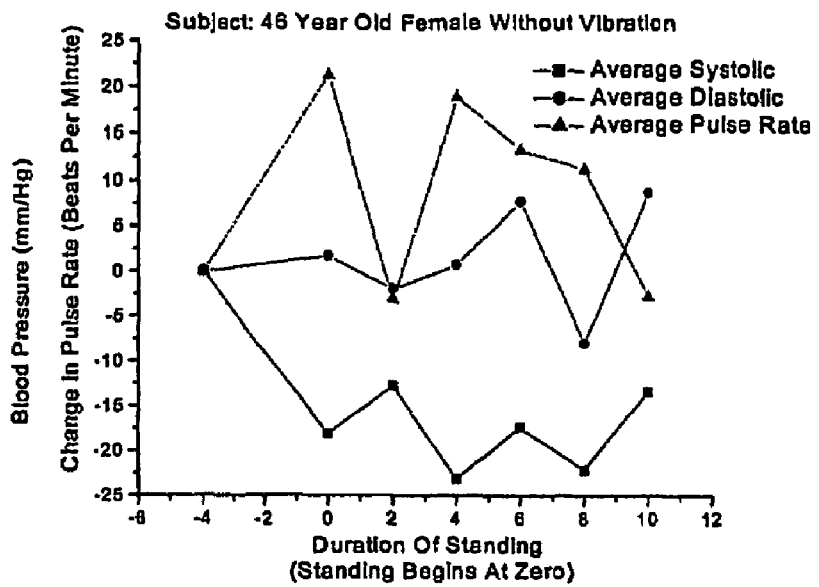
FIGS. 3 and 4 are graphs showing the influence of non-vibration and whole body vibration on several physiologic responses for a postmenopausal woman.

The response to orthostatic stress in the older individual is decidedly different from that observed in the younger individual. In the case of the 46 year old woman, as shown by FIG. 3, systolic blood pressure decreases substantially on standing, and this is compensated by an abrupt increase in pulse rate. There appears to be little evidence of any significant increase in diastolic blood pressure suggesting that peripheral resistance is not increasing, i.e., the individual is lacking both adequate skeletal muscle pump and vaso-constrictive activity. The declining systolic blood pressure in the absence of any corresponding significant rise in diastolic blood pressure and/or pulse rate indicates the potential for significantly pooling of blood in the lower extremities. Accordingly, the older adult female is experiencing orthostatic hypotension from maintaining a static posture.

Figure 4:
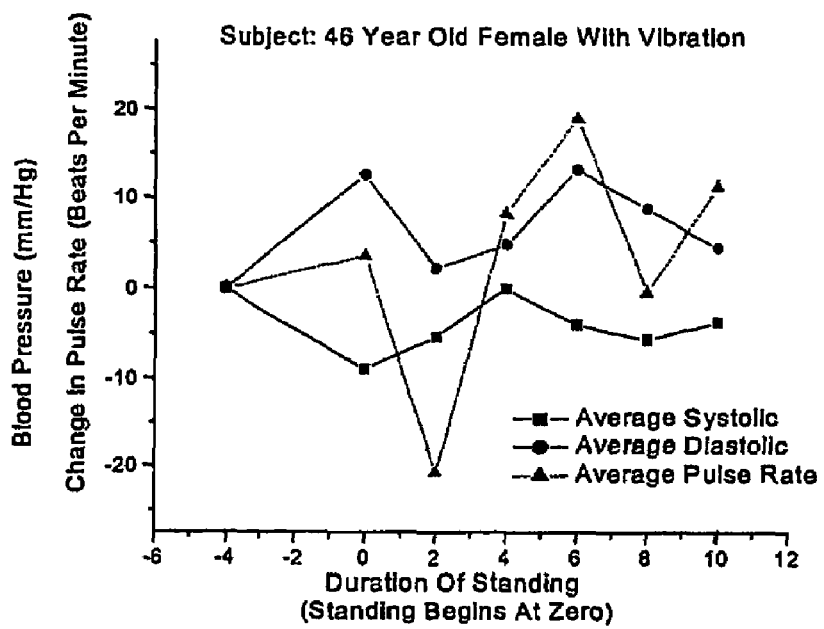

With reference to FIG. 4, exposure of this woman to vibration results in improvement in the physiologic response to orthostatic stress. In the presence of vibration, systolic blood pressure drops negligibly; conversely, diastolic blood pressure increases abruptly and is sustained. Pulse rate appears to be undergoing a slow increase over the twelve minutes of recording.

Figure 5:
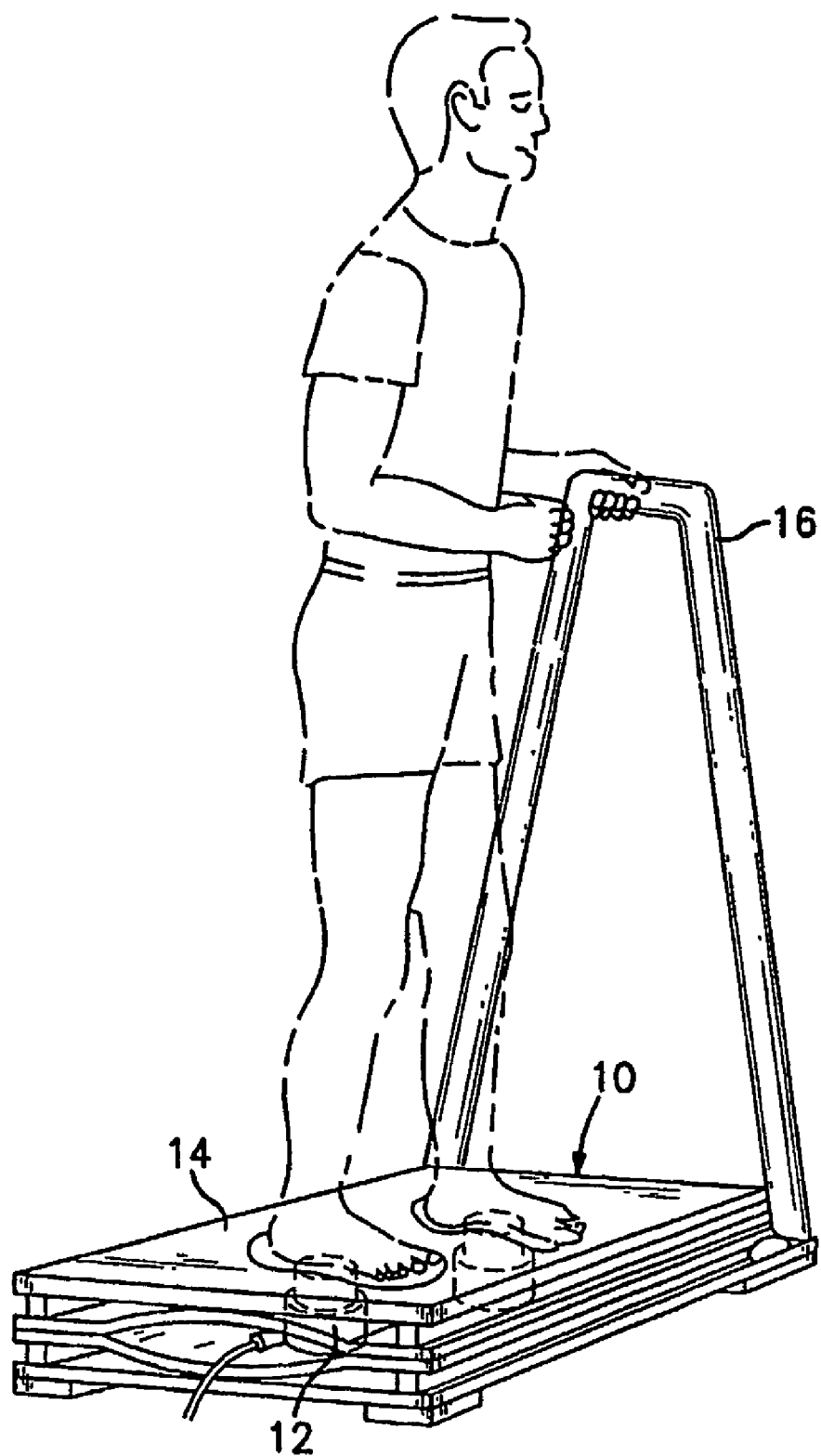
FIG. 5 is an isometric view showing a vibrating platform with a patient undergoing vibrational treatment for orthostatic hypotension in accordance with the method of the present disclosure.
Figure 6:
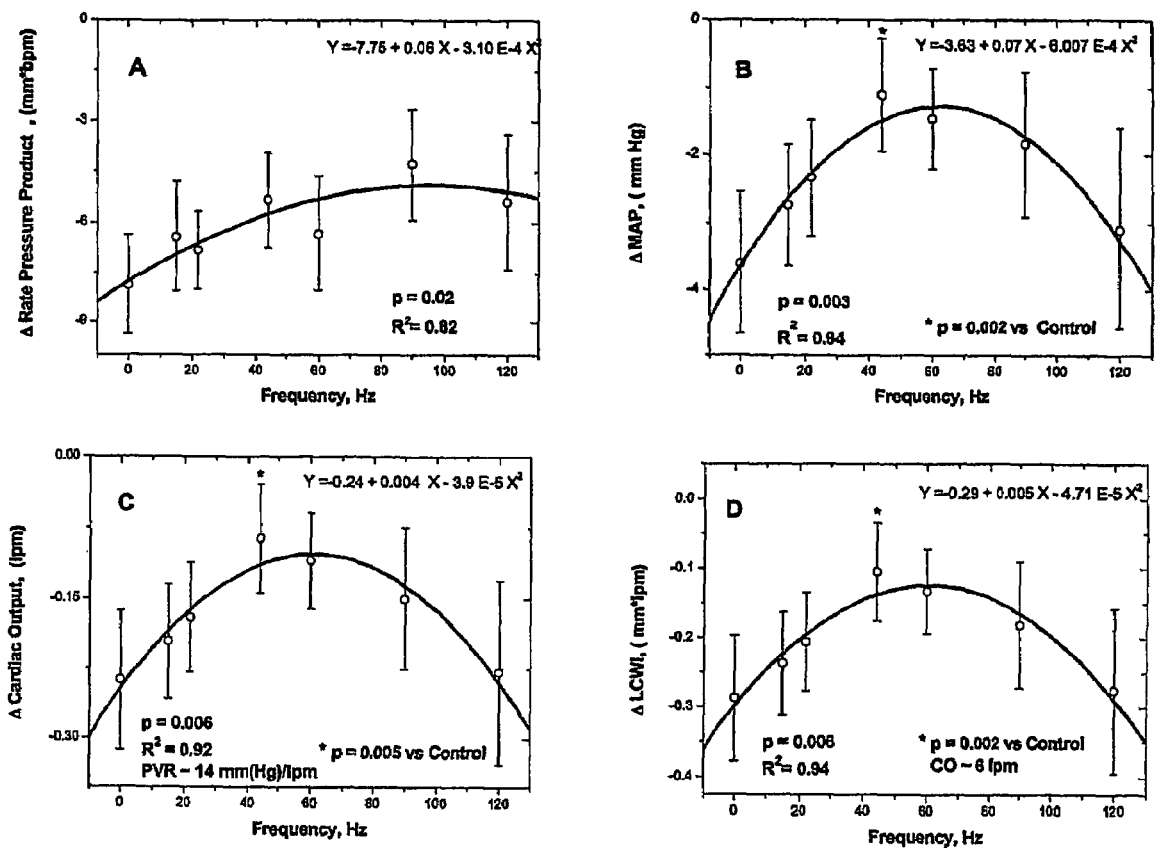
FIGS. 6A-6D are graphs showing the derived cardiovascular parameters as a function of vibration frequency for thirty individuals in the seated position.

In accordance with one method of the present disclosure, vibration applied to the base of the feet, or whole body vibration, using a vibration table 10 as shown by FIG. 5, is sufficient to stimulate neurosensory activity, resulting in a corresponding activation of the reflex arc resulting in sufficient muscle activity to ensure adequate blood and interstitial fluid return to the heart. The effect of the foot-based vibration, therefore, extends beyond sustaining an adequate nutrient flow to the lower limbs, thereby sustaining nerve, muscle and bone tissue in those regions, but also to upper body and cerebral activities.

FIG. 5 shows an individual undergoing the treatment method according to the present disclosure. The individual stands on the vibration table 10. Vibrations, generated by table 10 for a predetermined period of time, for example, 10 minutes, are transmitted through the individual's body. The vibrations are generated by motorized spring mechanisms 12 located underneath a standing platform 14 of the vibration table 10 and attached thereto. It is contemplated that the vibrations may be generated by a plurality of non-motorized springs or coils attached underneath the standing platform 14, upon which the standing platform 14 rests.

The frequencies imparted by vibration table 10 are in the range between 10-120 Hz with the acceleration of the vibration being in the range of 0.1 g/cycle to 1.0 g/cycle (where $g=9.8$ m/s$^2$), and preferably 0.1 g/cycle to 0.2 g/cycle, in order to cause the skin surface to be depressed by 10-50 microns. Preferably, the frequency of the vibration table 10 is in the range of 40-60 Hz. The vibration waves are preferably sinusoidal, however other waveforms are contemplated. The vibration can be uniform, interrupted, varying in magnitude, etc.

The frequency of vibrational loading of the standing platform 14 can be easily adjusted to permit focused treatment on specific mechano-receptors in the postural control process, i.e., cutaneous receptors, golgi tendon organs, muscle spindles, etc. The amplitude of vibrational loading of the standing platform 14 can be easily controlled from 0.05 to 0.5 g.

On the surface of the feet, the dominant sensory systems involve the Ruffini corpuscles, the Meisner corpuscles, and the Pacinian corpuscles. In addition, the golgi tendon organs and muscle spindles in the lower limbs could play an important role in the sensory transduction process.

Because five different sensory systems may be playing the dominate role in the detection of foot-based vibration and its influence on skeletal muscle pump activity, and correspondingly, the cardio-vascular system, a series of frequency sweep studies were undertaken to characterize the frequency response characteristics of the physiologic responses observed. Because each sensory system manifests distinct frequency response characteristics, this would allow the identification of the most important contributors to skeletal muscle pump control.

Thirty health female volunteers (age 30-80) participated in this study. Each was treated to seven distinct vibration exposures, extending from 0-120 Hz, each at 0.2 g (where $g=9.8$ m/$^2$). Specific treatment frequencies included: 0, 15, 22, 44, 60, 84, and 120 Hz. All treatments were with the subjects in a seated position with the feet (no shoes) placed on the vibration platform. Exposures were for twenty minutes. Systolic and diastolic blood pressure was taken before and after the vibration treatment. Heart rate was monitored continuously during the treatment Based on these measurements, four common derived cardiovascular parameters could be determined: change in the heart-rate pressure product; change in the mean arterial pressure; change in cardiac output; and change in left cardiac work.

The results shown by FIGS. 6A-6D clearly demonstrate how low-level vibration at the feet (with the subject in a seated position) is capable of significantly inhibiting the effects of orthostatic stress. In addition, the distinct frequency dependence of the cardiovascular response is evident, with the peak sensitivity occurring in the vicinity of 40-60 Hz range for the Mean Arterial Pressure (MAP) and related parameters, and in the range of 60-90 Hz for the rate pressure product. In the range of 40-60 Hz, calculations of MAP show that the physiologic response to orthostatic stress (upright quiet sitting) can be almost completely eliminated by the low level (0.2 g) foot-based vibration.

In these experiments, whole body vibration was utilized as a stimulus, however, as the skeletal muscle pump response does not require whole body vibration, but only stimulation of the vibration sensory systems in the lower limbs, it is clear that the apparatus of the present disclosure which is described below with reference to FIGS. 7 and 8 can stimulate the vibration sensory systems in the lower limbs, and subsequently, skeletal muscle pump activity, and can produce a similar response.

The main objective or purpose of the apparatus of the present disclosure is to achieve displacements in the range of at least 10 micrometers at the soles of the feet or other lower extremity body part, in the frequency range of 10-120 Hz, and preferably, in the range of 40-60 Hz, and that these frequencies be sustained for a predetermined period of time, e.g., two-minutes to twenty minutes, while the individual is in a substantially static posture as determined by at least one mechanical displacement sensor.

Figure 7:
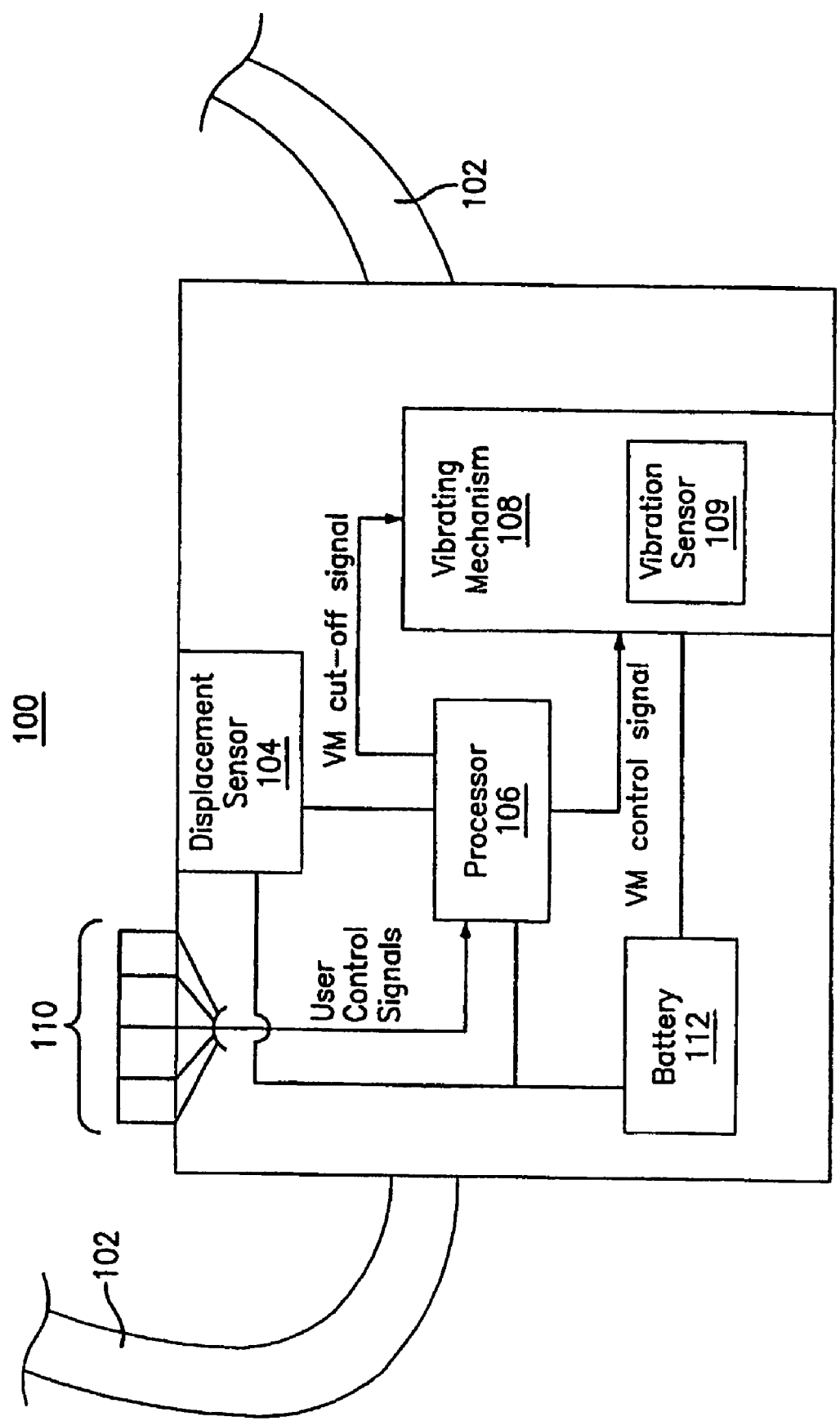
FIG. 7 is block diagram of an apparatus for treating orthostatic hypotension in accordance with the present disclosure.
Figure 8:
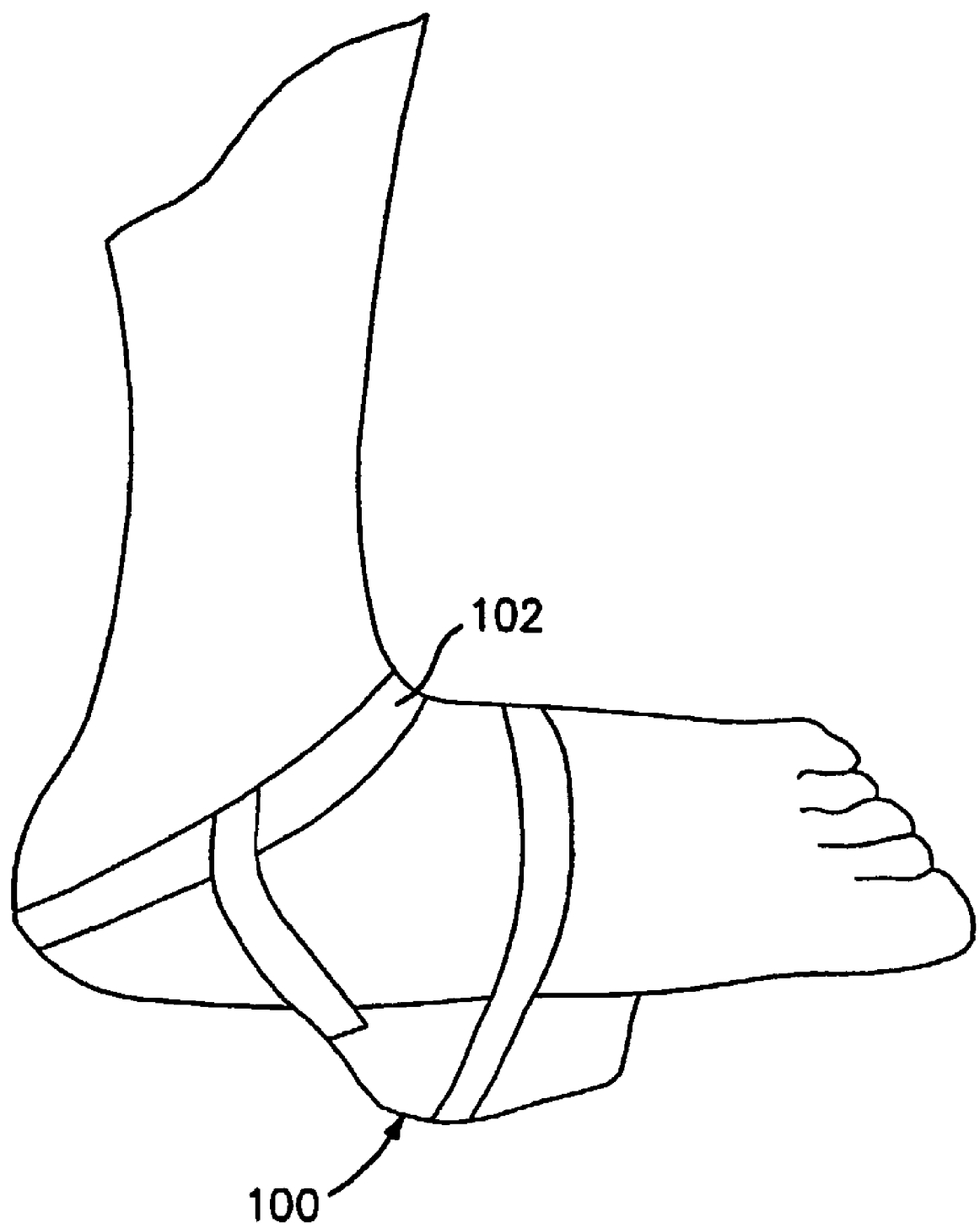
FIG. 8 is an enlarged perspective view of a patient's foot configured to be subject to vibrational treatment for orthostatic hypotension using the apparatus of the present disclosure.

With reference to FIGS. 7 and 8, the apparatus 100 includes a strap assembly 102 (or other fastening assembly) for being secured to a body part of the individual's lower extremity, such as the sole of one's foot as shown by FIG. 8, and a displacement sensor 104 which senses any substantial movement of the body part. The displacement sensor 104 continuously sends signals to a processor 106 of the apparatus 100 which indicate whether there was any substantial movement, e.g., more than 10 cm, of the body part. If the displacement sensor 104 did not sense any substantial movement of the body part for a predetermined period of time, e.g., five minutes, it is determined by the processor 106 that the person is in a substantially static posture and the processor 106 sends a vibrating mechanism control signal, VM control signal, to a vibrating mechanism 108.

The VM control signal activates the vibrating mechanism 108 causing at least one vibration sensor 109 within the vibrating mechanism 108 to vibrate, thereby imparting a vibrational force to the body part for vibrating the body part and resulting in enhanced blood and fluid flow in the lower extremities as described above. The vibrating mechanism 108 causes vibration of the body part for a predetermined period of time, e.g., two minutes to twenty minutes, or until body motion is detected by the displacement sensor 104. The vibration can be uniform, interrupted, varying in magnitude, etc.

After the predetermined period of time, the processor 106 sends a cut-off vibrating mechanism signal, VM cut-off signal, to the vibrating mechanism 108 to deactivate the vibrating mechanism 108 to cease vibration of the body part. The process then repeats itself on a periodic or irregular basis until the displacement sensor 104 senses movement of the body part or the individual uses controls 110 to turn off the apparatus.

The controls 110 on the apparatus 100 further enable the individual to select and set the predetermined periods of time and other parameters, such as the frequency that the vibrating mechanism vibrates, as well as to turn off the apparatus 100. The set parameters are transmitted to the processor 106 as user control signals. The processor 106 uses the user control signals to control the apparatus 100 according to the user-selected settings.

The controls 110 can also be used to bypass the automatic activation of the vibrating mechanism 108 by the processor 106 transmitting the VM control signal if the displacement sensor 104 does not sense any substantial movement within the predetermined period of time. That is, the controls 110 can be used to cause direct electrical stimulation of the vibrating mechanism 108, thereby, bypassing the mechanical displacement sensor 104, allowing a robust response even in the elderly who have lost much, if not most, of their vibro-tactile sensation abilities.

It is provided that the controls 110 can be located on a wireless or non-wireless remote control for enabling the individual to easily control the apparatus 100 by controlling the operation of the processor 106 while in any body position and in any condition. It is further provided that the processor 106 includes a set of programmable instructions within a storage module which are capable of being executed by the processor 106 for enabling the apparatus 100 to perform its functions. The apparatus 100 further includes a battery compartment (not shown) for placement of a battery 112 therein for powering the various components of the apparatus 100.

For optimum results, it is noted that two apparatuses, one secured to one lower extremity and other secured to the other lower extremity, operating simultaneously should be utilized.

It is contemplated for the soles of the feet to be bypassed and the neuromuscular system be stimulated at the level of the Achilles' tendon, triggering skeletal muscle activity. It is further contemplated to stimulate the muscle body itself to directly produce muscle twitching, and therefore, skeletal muscle pump activity. Further, it is contemplated to embody the apparatus within footwear, such as a shoe or sock, for easily placing the apparatus in proximity to the sole of one's foot during treatment.

Potential application of the described method and apparatus is envisioned in occupational, healthcare, or home settings where extended periods of quiet standing or seating is required and which could result in significant decreases in physical and mental fatigue, as well as other pathophysiological responses associated with decreased blood and fluid flow, including, for example, the disuse related bone and muscle loss arising from the poor perfusion caused by these static postures.

The method and apparatus of the present disclosure enable the individual to be treated for orthostatic hypotension in any setting and while performing virtually any activity, such as typing and being a passenger in an aircraft, train, automobile, or other vehicle, as well as when the individual is sleeping or resting. Other advantages provided by the method and apparatus of the present disclosure is that little or no training/learning is required of the individuals; the apparatus is inexpensive to construct and its small size and low weight make it convenient for concealment, storage and use; only a short duration of treatment is required for significant effect (approximately two minutes per vibrational period); the treatment method using the apparatus can be performed while the patient is in the standing, seated, or any other upright static posture; and the apparatus can be used to treat the infirm elderly where other treatments for orthostatic hypotension are beyond the physical capabilities of these individuals.

Although this disclosure has been described with respect to preferred embodiments, it will be readily apparent to those having ordinary skill in the art to which it appertains that changes and modifications may be made thereto without departing from the spirit or scope of the disclosure.

What is claimed is:

1. A wearable apparatus for treating orthostatic hypotension, said apparatus comprising:
    a vibration mechanism configured for imparting a vibrational force to a body part of a lower extremity of an individual during treatment for a period of time and at at least one frequency sufficient for therapeutic affect on orthostatic hypotension;
    a processing unit for controlling activation of the vibration mechanism in response to at least one signal received from a displacement sensor upon sensing non-movement of the body part or from a manually settable control; and
    a securing mechanism for securing said apparatus to said body part, wherein said apparatus is configured and dimensioned for being concealed during operation thereof.

2. The apparatus according to claim 1, wherein said vibration mechanism is provided below a vibration platform for vibrating the vibration platform for the period of time and at the at least one frequency to impart the vibrational force to said body part situated on said vibration platform.

3. The apparatus according to claim 1, wherein the period of time is in the range of two to twenty minutes.

4. The apparatus according to claim 1, wherein the manually settable control includes means for setting the period of time and the at least one frequency.

5. The apparatus according to claim 1, wherein the at least one frequency is in the range of 10-120Hz.

6. The apparatus according to claim 1, wherein the at least one frequency is in the range of 40-60Hz.

7. The apparatus according to claim 1, further comprising a set of programmable instructions configured for execution by the processing unit for activating the vibration mechanism on a periodic or irregular basis.

8. The apparatus according to claim 1, further comprising remote control means for remotely controlling said processing unit.

9. The apparatus according to claim 1, wherein the acceleration of the vibration is in a range of 0.1 g/cycle to 0.2 g/cycle to cause the skin surface of the body part to be depressed by 10-50 microns.

* * * * *